United States Patent [19]
Allen

[11] Patent Number: 5,824,013
[45] Date of Patent: Oct. 20, 1998

[54] SPINAL BRACE FOR CORRECTING LORDOSIS

[75] Inventor: Dillis V. Allen, Elgin, Ill.

[73] Assignee: Vardon Golf Company, Inc., Elk Grove Village, Ill.

[21] Appl. No.: 364,667

[22] Filed: Dec. 27, 1994

[51] Int. Cl.$^6$ ..................................................... A61F 5/00
[52] U.S. Cl. ........................... 606/240; 128/845; 5/471; 5/481; 5/643
[58] Field of Search ........................... 128/845; 601/121; 606/237, 240; 482/130, 133; 5/491, 643, 636, 470, 471, 481, 490; 206/397, 401, 410, 417

[56] References Cited

U.S. PATENT DOCUMENTS

| | | | |
|---|---|---|---|
| 2,883,045 | 4/1959 | Abramson | 206/410 X |
| 2,943,621 | 7/1960 | Phillips et al. | 601/57 |
| 3,378,860 | 4/1968 | Frazier | 5/491 |
| 3,419,268 | 12/1968 | Bellet | 601/121 X |
| 3,705,579 | 12/1972 | Morini et al. | 601/121 |
| 3,719,185 | 3/1973 | Hanes | 606/240 |
| 3,750,654 | 8/1973 | Shiu | 601/121 |
| 3,842,453 | 10/1974 | Redfield | 601/121 X |
| 4,081,870 | 4/1978 | Iannucci | 5/491 X |
| 4,519,605 | 5/1985 | Leland | 601/121 X |
| 4,761,872 | 8/1988 | Buettner et al. | 5/636 X |
| 4,911,299 | 3/1990 | Peeters | 206/410 |

*Primary Examiner*—Linda C. Dvorak

[57] ABSTRACT

A spinal brace and exercise implement for the human spine, and particularly its cervical, thoracic and lumbar regions, including a rigid cylindrical base surrounded by a high deflection factor foam material.

3 Claims, 6 Drawing Sheets

5,824,013

SPINAL BRACE FOR CORRECTING LORDOSIS

BACKGROUND OF THE INVENTION

The central support for the entire body is the spine, also known as the backbone. It actually consists of many small bones called vertebrae. They are held together by ligaments. The ribs curve out from the vertebrae of the chest cavity. Because the lower vertebrae bear more weight, they are thicker and heavier than the vertebrae higher up.

Running through the back part of the vertebrae is the spinal cord, an important organ of the nervous system. The cord is about 18 inches (45 centimeters) long in an adult, reaching from the brain to just below the lowest vertebra of the chest cavity.

Between each two vertebrae is a disc of softer cartilage. These spinal discs are shock absorbers for the delicate brain at the top of the spine. When one sits or stands, the discs are squeezed together. This accounts for total body height being about one-fourth to one-half inch shorter before you go to bed than when you get up.

Because the spinal discs are somewhat flexible, they allow one to bend and turn the backbone in many directions. One can reach for a book on a high shelf, bend down to tie shoelaces, or swing a tennis racket.

Sometimes a disc will squeeze out beyond the vertebrae, pressing painfully on a nearby nerve. This is called a slipped disc. Bed rest may ease the pain and strengthening the back muscles may compensate for the weakness of the disc.

The normal curvatures of the vertebral column are very important for the flexibility of an upright posture; a straight column would not be so flexible. However, the curvatures are sometimes abnormally pronounced, or veer from the midline, and some of the skeletons that one will see in the laboratory may show one or more of these deformities. Common deformities are: kyphosis, an exaggerated thoracic curvature; lordosis, an exaggerated lumbar curvature; and scoliosis, a curvature that veers to either side of the midline of the body (a lateral curvature).

As noted above, the vertebral column is not perfectly straight when viewed from the side. It moves slightly inward in the neck, outward in the chest, and inward again in the lower back. However, it is straight when viewed from the rear. In some people because of disease, and sometimes even because of poor posture, and in some cases trauma, the curvature becomes distorted.

In one case commonly called "hunchback", technically known as kyphosis, the thoracic region of the spine curves too far outwardly. In another condition, the inward curvature of the cervical and lumbar regions, commonly referred to as normal lordosis, becomes abnormal either by too much or too little curvature, and this condition is called simply lordosis, albeit somewhat inaccurately. If the curvature is excessive, it is referred to as hollow back, subtle back and sway back.

The term "scoliosis" means abnormal vertical curvature where the spine is curved instead of straight up and down when viewed from the rear.

The cervical conditions to which the present invention is principally directed is the straightening of the cervical and lumbar spines from the normal lordosis.

It is known in the orthopedic and chiropractic fields to provide external support devices in each of the two principal spinal curves, namely the cervical region and the lumbar region. These devices usually take the form of relatively soft pillows or rolled up towels. Examples of such support devices are shown and described in the following patents:

U.S. Pat. No. 2,943,621
U.S. Pat. No. 3,234,569
U.S. Pat. No. 3,842,453
U.S. Pat. No. 4,431,232
U.S. Pat. No. 4,761,872
U.S. Pat. No. 4,835,801
U.S. Pat. No. 5,148,564
U.S. Pat. No. 5,152,019

These spinal curvature supporting devices actually provide very poor support, and insofar as I am aware, have not heretofore been utilized as spinal exercise and massaging devices. These prior spinal curvature supporting devices are in some cases circular in cross-section, some rectangular, and some with irregular cross-sections obstensibly conforming to natural body contours. The principal reason that these prior supporting devices are ineffective is that they are incapable of exerting the necessary degree of pressure in the cervical and lumbar regions to brace and hold the spine from its somewhat straightened position back to normal lordosis. This incapability is attributed directly to the composition and construction of these prior supporting devices which are actually nothing more than pillows. All of the supporting devices which I am aware are bendable along their horizontal axes and have a fairly consistent resilient material construction that extends entirely through their cross-section.

It is a primary object of the present invention to ameliorate the problems noted above in providing support for bracing the human spine and particularly the curved regions thereof that is light-weight, mobile and easy for the patient to handle and use.

SUMMARY OF THE PRESENT INVENTION

In accordance with the present invention, an improved orthopedic brace and exercise implement is provided for the human spine and particularly its curved cervical and lumbar regions although its uses are not limited to these regions. This brace, and implement, includes a rigid cylindrical tube defining a base that is surrounded by a high deflection factor foam material.

The tube in one embodiment is a polyvinyl chloride (PVC) resin tube and the rigid foam has a density in the range of 1.2 to 3.0 lbs. per cubic foot and an ASTM foam deflection factor in the range of 45 to 85.

The foam is covered by an upholstery type material that not just provides increased user comfort but increases the firmness in the foam because it has an interfering fit with the outer diameter of the foam material. Both the foam and the cover are wrapped inside the ends of the tube to provide a cushioning effect for the tube ends and to of course aesthetically finish the product. The remaining apertures in the ends of the assembly are covered by a pair of opposed button assemblies that are drawn together with an appropriate cord extending centrally through the tube assembly.

The principal construction element of the present orthopedic brace distinguishes it from prior art pillow-type supports, is that the present brace is completely inflexible along its longitudinal axis; that is, under normal body forces, even in the 300 lb. range, the brace assembly cannot be bent along the normal relaxed straight longitudinal axis of its base tube. And while the brace can be compressed somewhat radially perpendicular to that longitudinal axis because the foam is deformable, the amount of that radial deflection at any point along the longitudinal axis of the brace is limited by the sum of the radius of the rigid tube and the fully compressed thickness of its surrounding foam. It is these physical characteristics of the present brace that give it the capability of exerting sufficient pressure on the spine to return it toward normal lordosis and hold it in that position for whatever period of time the individual desires.

This tubular orthopedic brace assembly is utilized by the patient to reduce stress in the lumbar spine while in the sitting position by placing it horizontally between the lumbar spine and an adjacent seat backrest. Because of its non-attachment to either the body or the seat backrest, it can be placed in a variety of positions in the lumbar region enabling the patient to shift the device from one vertical position to another to obtain the greatest stress relief and the desired lumbar pressure.

This brace can also be used to exercise the lumbar region in the sitting position with the brace placed between the lumbar region and the seat backrest. To begin the exercise, the patient's back is initially erect and then the patient rocks forward at the shoulder. This motion rolls the cylindrical brace upwardly a fractional turn massaging the vertebrae discs and associated ligaments and muscles and increasing blood flow in the area. The patient then rocks the shoulders back to their vertical position and this motion causes the cylindrical brace to roll downwardly back to its original position in the lumbar region.

The brace can also be used in a similar manner in the prone position to exercise and massage the lumbar region and the cervical region as will be described in more detail in the detailed description of the invention.

The stress relieving and massaging benefits of this very unique orthopedic brace are directly attributed to its rigid cylindrical base. The use of a rigid tube, however, by itself would damage and bruise tissue, muscles and ligaments and perhaps even the spinal bones themselves, and hence, it is necessary that some cushioning be provided between the rigid tube and the body surfaces. The amount of cushioning, however, is very important to the present invention because too much cushioning negates the benefits of the rigid brace to the human spine and too little cushioning may exacerbate the already existing spinal stresses.

The present orthopedic brace is embodied in two sizes: one referred to as a regular, and the other as a large. The regular brace is designed for lighter weight and smaller patients, as well as the cervical areas for all sized patients, and the large is particularly suited for lumbar support and exercise in larger or overweight patients.

In the large brace, the rigid tube has an outer diameter of 2⅜th inches, foam thickness of 1¼ inches, foam density in the range of 2.0 to 3.0 lbs. per cubic foot and an ASTM foam deflection factor in the range of 50 to 80. Of course there are variations in these parameters in the range of plus or minus 20% which have been found to provide adequate stress relieving results without exacerbating stress, but these have been found to be optimal.

In the regular size brace, the rigid tube has an outer diameter of 1⅞th inches, a foam thickness of ¾ inches with foam density and deflection factors the same as in the large version.

Other objects and advantages of the present invention will appear more clearly from the following detailed description.

DETAILED DESCRIPTION OF THE PREFERRED EMBODIMENT

Figure 1:
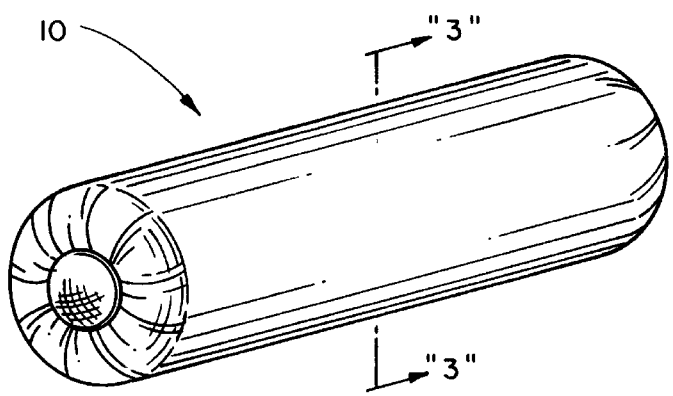
FIG. 1 is a perspective view of the large embodiment of the present spinal brace.
Figure 2:
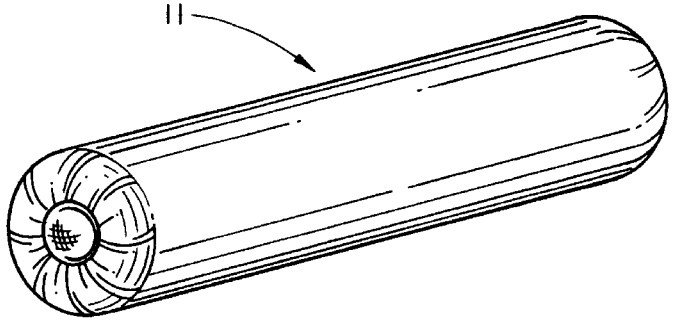
FIG. 2 is a perspective view of the regular embodiment of the present spinal brace slightly smaller in diameter but not in length than the spinal brace illustrated in FIG. 1.

Referring to the drawings, and particularly FIGS. 1 and 2, a spinal brace 10 according to the present invention is illustrated in FIG. 1 and a spinal brace 11 is illustrated in FIG. 2, both of which embody the principles of the present invention. It should be understood that while the brace assembly according to the present invention is termed a "spinal" brace, that it has applications for correcting and exercising other portions of the human anatomy; i.e., other than the spine, notably the knee area and the foot area as will appear more clearly in this detailed description.

Without going into great detail with respect to the differences between the brace 10 and the brace 11 at this early point in the description of the invention, it can be briefly said that both have a length of approximately 13 inches with the large diameter brace 10 having an outer diameter of approximately 4⅞ths inches and the smaller diameter brace 11 having an outer diameter of approximately 3⅜ths inches. Each of the braces 10 and 11 can be used for all of the recommended spinal brace uses and exercises and the difference between the two is largely determined by the patient's physical characteristics, notably patient size, patient overweight or underweight, and the degree of abnormality in the correction areas. Other than the diameters of the various sub-assemblies, the brace 11 is identical to the brace 10 as will appear below.

Figure 3:
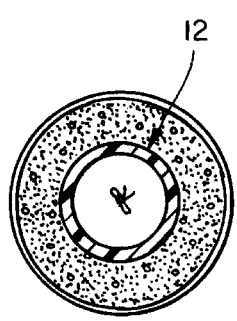
FIG. 3 is a cross section through the spinal brace illustrated in FIG. 1 taken generally along line 3—3 thereof.
Figure 7:
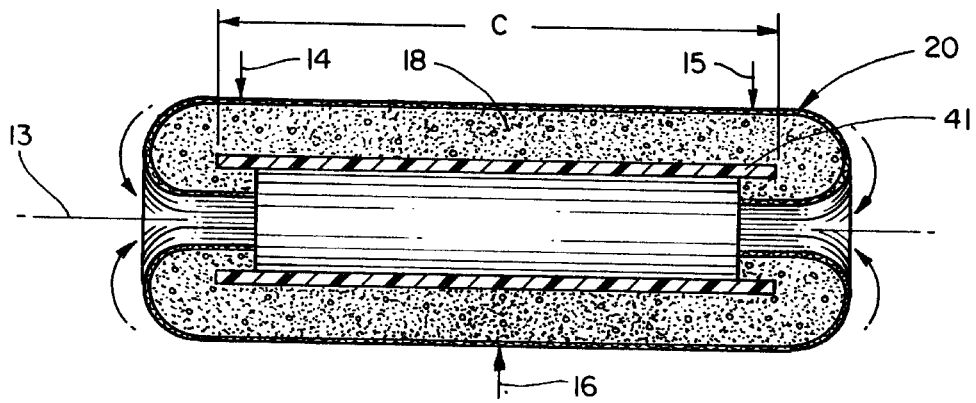
FIG. 7 is a longitudinal section of the spinal brace illustrated in FIG. 1 with the rigid tube length designated by the alpha C.

As seen in FIGS. 3 and 7, the brace assemblies 10 and 11 include a rigid inner tube 12 that provides complete axial rigidity to the braces 10 and 11 distinguishing these braces from all pillow-type orthopedic supports. That is, the tube 12 as illustrated in FIG. 7, prevents the straight longitudinal axis 13 from bending out of its straight line configuration illustrated in FIG. 7 by the simultaneous application of forces to the brace at points 14, 15 and 16, and that is referred to herein as longitudinal rigidity. The tube 12 has a dimension "C", its axial length, in both embodiments 10 and 11 of approximately 12 inches. Also, in both embodiments the wall thickness of tube "C" is on the order of 3/16ths inches.

The tube 12 is constructed of a high impact rigid polymer such as polyvinylchloride (PVC), and its length designated "C" in FIG. 7 is as noted approximately 12 inches in both the braces 10 and 11.

A foam sheet 18 is glued around the tube 12 and is preferably a polyurethane foam of aircraft upholstery grade. One such foam that has been found particularly suitable is a closed cell polyurethane foam having a density of 2.8 lbs. per cubic foot, and an ASTM deflection factor of 60. However, testing has indicated that foams having a density in the range of 2.0 to 3.0 lbs. per cubic foot, and an ASTM deflection factor in the range of 50 to 75 provide acceptable results. The purpose of the foam layer(or sheet 18 prior to assembly) is two-fold. Firstly, it provides user comfort by isolating the hard exterior surface of the tube 12 from the patient's boney skeletal areas, such as along the spine, that are not protected by thick areas of flesh or muscle. The second purpose of the foam sheet 18 is to transmit the unyielding forces of the rigid tube 12 in a somewhat muted fashion to the patient's skeletal area to be treated. Thus, the density, deflection factor, as well as the radial thickness of the foam sheet or tube in its assembled condition, are balanced to provide the maximum rigid bracing and pressure effort possible consistent with patient comfort or expressed otherwise, without patient discomfort. Foam thickness in brace 10 is 1.5 inches and in brace 11 is 3/4 inches.

Figure 6:
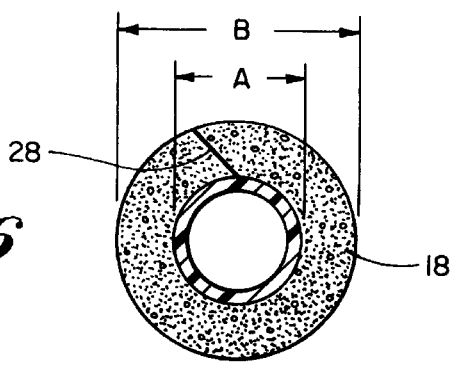
FIG. 6 is a cross-section of the rigid tube and foam assembly with A and B dimensions designated.

Viewing the dimensional relationships illustrated in FIG. 6, the outer diameter "A" of the tube 12 in brace 10 is on the order of 2 3/8ths inches and in brace 11 is 1 7/8ths inches. The outer diameter "B" of the tube and foam assembly illustrated in FIG. 6 is on the order of 4 7/8ths inches in the brace 10 and 3 3/8ths inches in the brace 11. Thus, the maximum deflection in the large diameter brace in a radial direction(with the foam at complete compression along a diametral line) is on the order of 51%, and on the regular brace, the maximum deflection is about 56%. Acceptable maximum deflections are found in the range of 45% to 60%. Maximum deflection for this purpose is defined as the outer diameter of the assembly less than the outer diameter of the rigid tube divided by the outer diameter of the assembly times 100.

While not shown in FIG. 6, a cover 20 surrounds the foam 18 for the purpose of providing increased user comfort as well as holding the foam sheet in the appropriate desired configuration. Buttons 22 and 23 close the ends of the tube, the foam and cover assemblies to finish the product and maintain its structural integrity.

The cover 20 is an upholstery weight and quality material that provides not only user comfort but an appropriate surface for product graphics such as by silk screening. In certain cases the cover 20 may take the form of a non-fabric material such as vinyl sheeting to provide a more washable product for certain applications such as outdoor use where washability is desirable.

Figure 4:
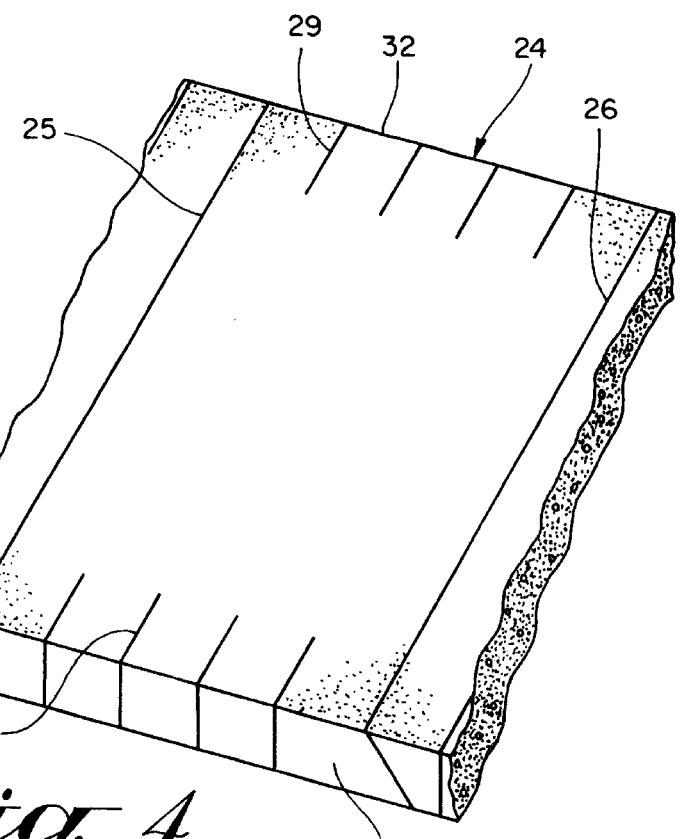
FIG. 4 is a fragmented perspective of a foam sheet cut in accordance with the present invention prior to assembly into the spinal brace.

The method of manufacturing the present braces will be described with reference to FIGS. 3 to 9, and initially viewing FIG. 4, a fragmented foam sheet 24 is illustrated representing the assembled foam tube 18 in its flat configuration. Prior to assembling the foam sheet to the tube 12, the flat foam sheet is cut at a 90 degree transverse line 25 at one end and a 45 degree line 26 at the other end providing the appropriate wrap-around length for the foam tube 18 illustrated in FIG. 6, and more specifically, providing a butt joint 28 where the ends of the foam sheet meet when rolled around tube 12. If both ends of the foam sheet are cut transversely at a 90 degree angle, the ends of the foam sheet 24 wrapped around tube 12 will not meet on a common line as at butt joint 28.

Also, a series of cuts 29 and 30 are made from the ends of the foam sheet inwardly a distance of approximately two inches. Sheet 24 has a width between ends 32 and 33 of approximately 18 inches.

Figure 5:
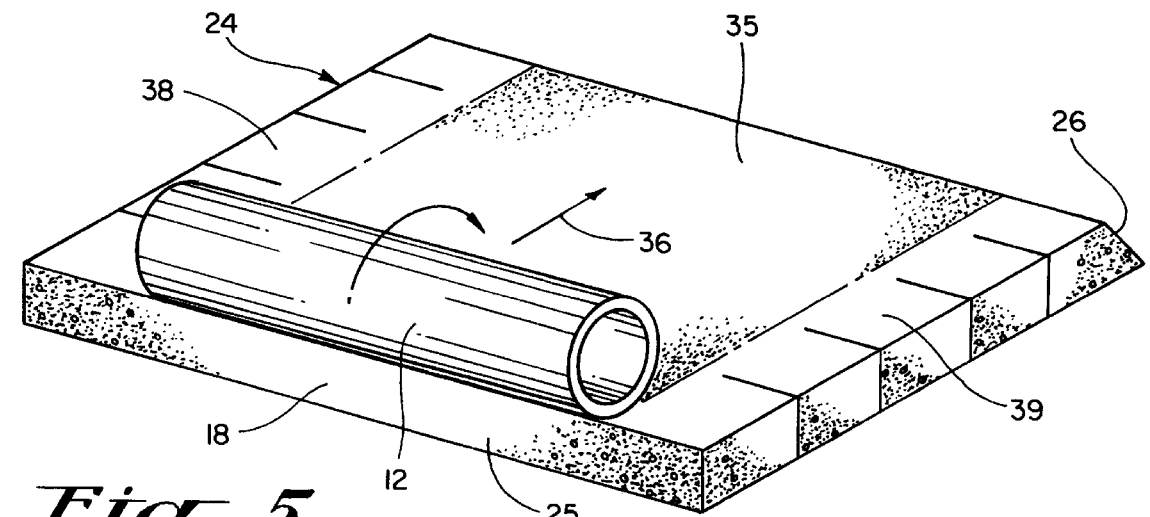
FIG. 5 is a perspective view illustrating one method of attaching the inner rigid resin tube to the outer foam sheet.

As seen in FIG. 5, the tube 12, after a suitable contact adhesive is applied to the outside surface of the tube and the top area 35 of sheet 24, is rolled in the direction of arrow 36 on the sheet joining the sheet and tube into the assembly illustrated in FIG. 6.

Thereafter, the fingers 38 and 39 at the ends of the foam tube 18 defined by the cut lines 29 and 30 are sequentially pushed inside the ends of the tube 18 and are glued as indicated at 41 in FIG. 7 to the inside of tube 12.

The cover 20 is cut and sewed prior to its assembly to the tube and foam assembly illustrated in FIG. 6. That is, it is cut to a width approximately the same as the foam; i.e., 18 inches, and sewed along a longitudinal line to a diameter slightly less, approximately 1/8th inch, than the relaxed diameter of the tube and foam assembly illustrated in FIG. 6. In this manner, the cover firms the outer surface of the foam somewhat and provides a very smooth assembly. The ends of the cover, preferably prior to sewing it to the appropriate diameter, are cut along lines similar to lines 29 and 30 in the foam sheet 18.

Figure 8:
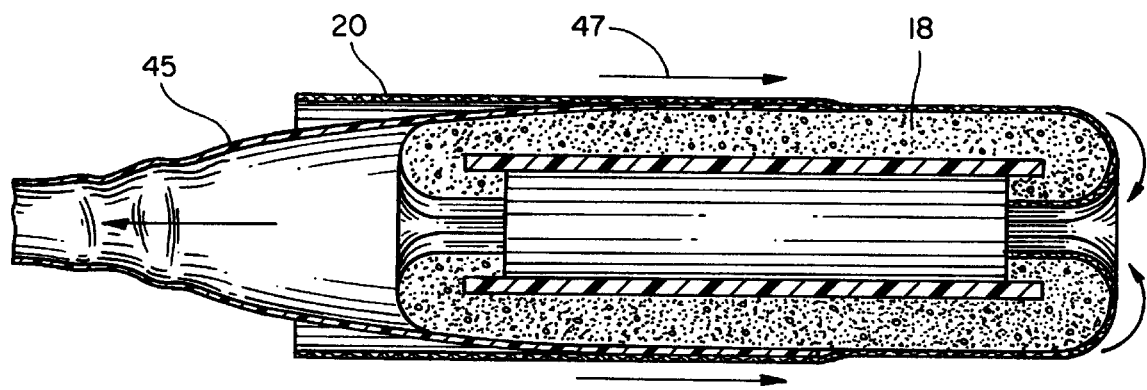
FIG. 8 is a longitudinal section of the present spinal brace and particularly the method of sliding the outer cover over the foam.

The cover 20 as illustrated in FIG. 8 is drawn over the foam 18 by first wrapping a low friction plastic film 45 around the foam 18 and then sliding the cover axially over the foam and sheet 45 in the direction illustrated by arrow 47 in FIG. 8. Sheet 45 eliminates the frictional resistance that the foam 18 would otherwise exert on cover 20 making it difficult to draw the cover 20 over the foam. After the cover 20 is drawn to its appropriate longitudinal position with respect to the foam and tube assembly, it can be held in position and the sheet 45 withdrawn from the assembly and reused.

Figure 9:
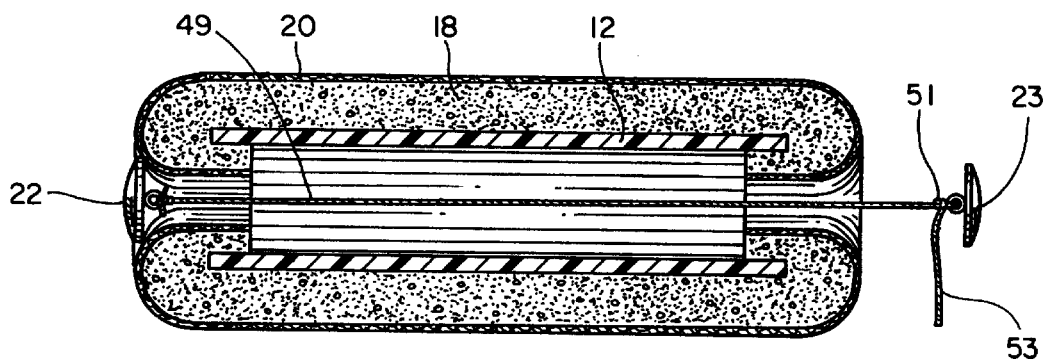
FIG. 9 is a longitudinal section of the present spinal brace illustrating the method of assembling the end buttons to the ends of the assembly.

As seen in FIG. 9, the button assemblies 22 and 23 are fastened to the tube, foam and cover assembly by attaching a nylon cord 49 to button 22, fishing the line through the brace assembly, slip-knotting as at 51 the line to button 23 and then by pulling on line 53 drawing button 23 against the right end of the assembly. Thereafter the end 53 is whipped around and half-hitched and then snipped off flush to button 23.

Figure 10:
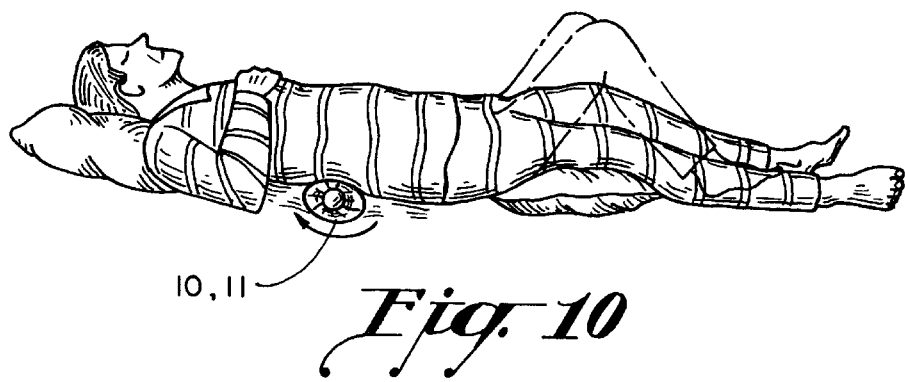
FIG. 10 illustrates a patient in the prone position effecting a lower lumbar exercise with the present spinal brace.

The first exercise for the present spinal brace is illustrated in FIG. 10 with the patient prone and pillows underneath the head and underneath the knee region with the present brace positioned in the lumbar area. This exercise should proceed with the patient lying on a very soft surface such as a bed. Either the brace 10 or the brace 11 can be utilized for this exercise depending upon the patient's size, weight, physical condition, as well as the firmness of the supporting surface. With the brace positioned as illustrated, the patient raises his or her knees up and down causing the brace 10, 11 to roll along the lumbar region in both directions as the knees are raised and lowered.

Figure 11:
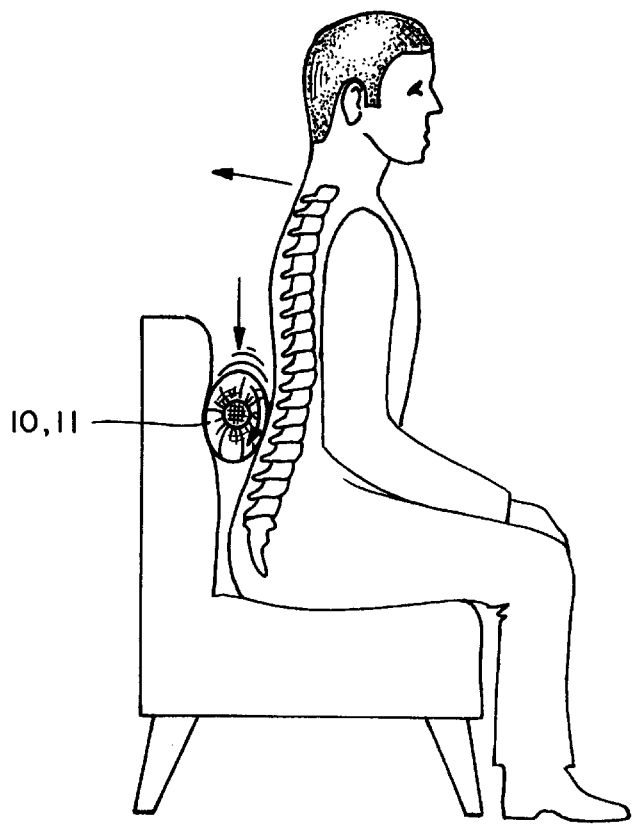
FIGS. 11 and 12 illustrate a patient in the sitting position effecting an exercise of the spinal lumbar region with the present spinal brace.
Figure 12:
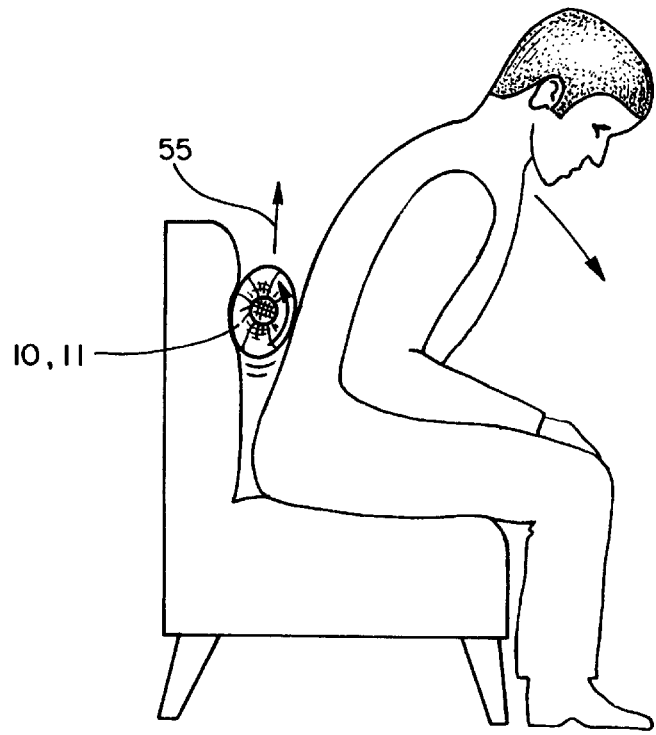

A similar exercise is illustrated in FIGS. 11 and 12 with the patient in a sitting position in a fairly smooth backed chair and the brace located in the spinal lumbar region transverse to the spine clamped between the chair back and the rear lumbar region of the patient. Beginning with the patient shown in a thoracic upright position shown in FIG. 11, the patient rocks forwardly from the shoulders to the position illustrated in FIG. 12 and this movement causes the brace 10, 11 to roll in a counter-clockwise direction upwardly in the direction of arrow 55 illustrated in FIG. 12. Thereafter, the patient rotates the thoracic region back to its upright position in FIG. 12 causing the brace 10, 11 to roll in a clockwise direction downwardly along the spine and on the chair backrest. The actual upward and downward movement of the brace is in a very narrow range in this exercise but still is of great benefit in increasing blood flow, massaging and reducing lordosis.

Figures 13, 14, 14A:
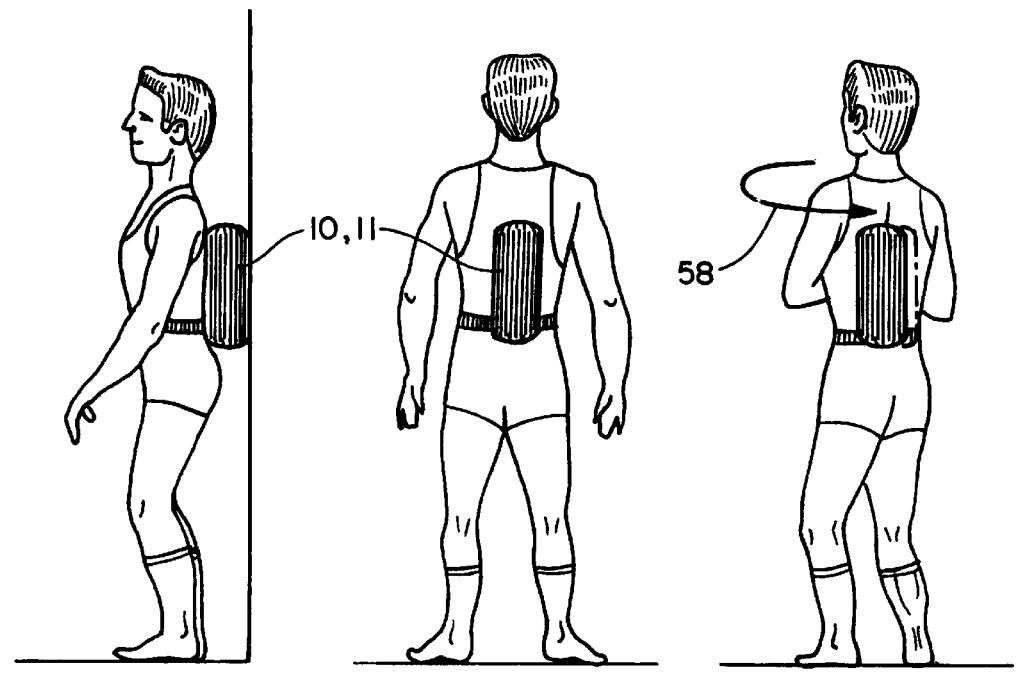
FIGS. 13, 14 and 14a illustrate the patient utilizing the present spinal brace in a thoracic spinal exercise.

In the exercise illustrated in FIGS. 13, 14 and 14a, the brace 10, 11 is placed in a vertical orientation between a wall and the patient's thoracic area parallel and in line with the spine. The patient then proceeds to rock from side to side as illustrated by arrow 58 in FIG. 14a causing the brace 10, 11 to roll on the thoracic back area in a direction opposite the direction of patient movement.

Figures 15, 16:
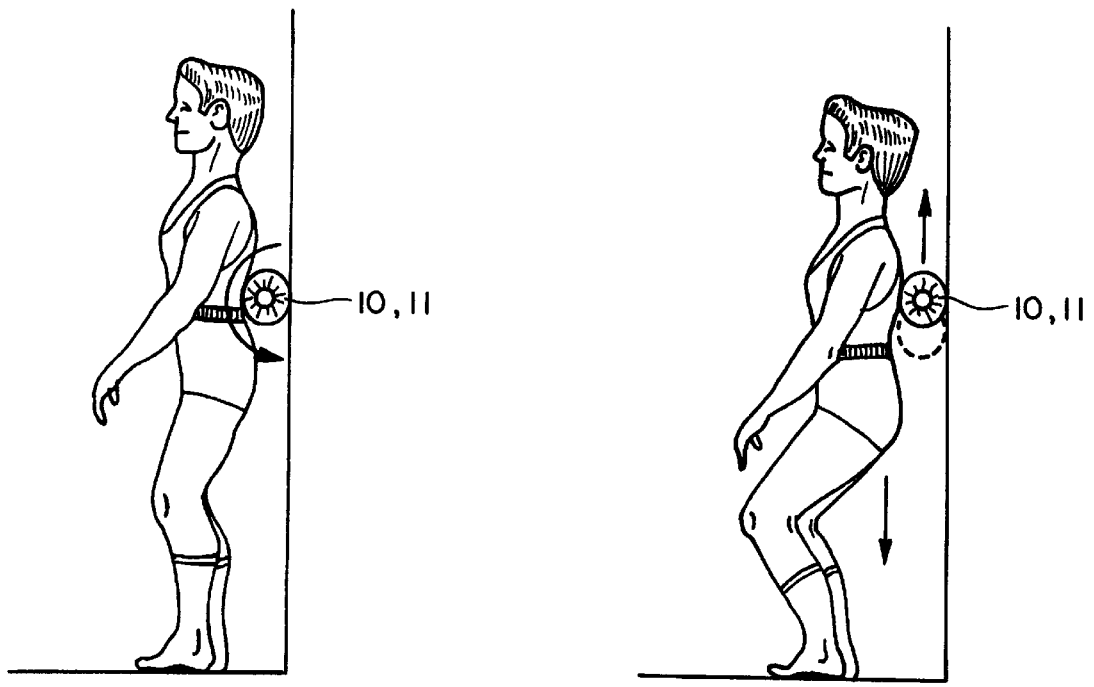
FIGS. 15, 16 and 17 illustrate the patient in standing-squatting positions exercising the lumbar and thoracic regions with the present spinal brace.
Figure 17:
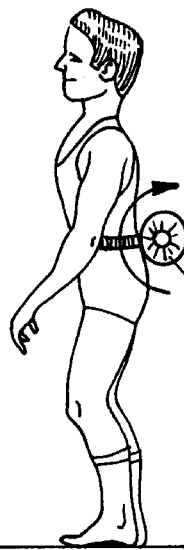

In the exercise illustrated in FIGS. 15, 16 and 17, the brace 10, 11 is positioned, with the patient standing erect as shown in FIG. 15, between a vertical wall and the patient's lumbar area. The patient then proceeds to do a partial or deep knee squat as shown in FIG. 17 causing the brace 11 (preferable in this exercise) to roll in a counterclockwise direction up the patient's spine through the thoracic area almost to the cervical area. The patient then straightens the legs raising the thoracic area as illustrated in FIG. 17 causing the brace 10, 11 to roll in a clockwise direction back down the patient's spine to the original lumbar area illustrated in FIG. 15.

Figure 18:
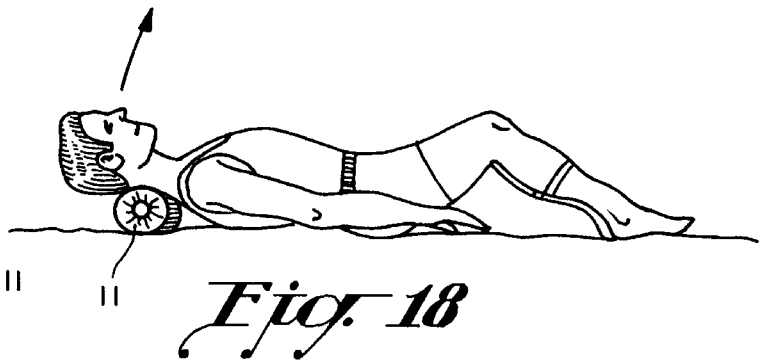
FIGS. 18, 19 and 20 illustrate the patient in a prone position utilizing the present spinal brace in a cervical spine exercise.
Figure 19:
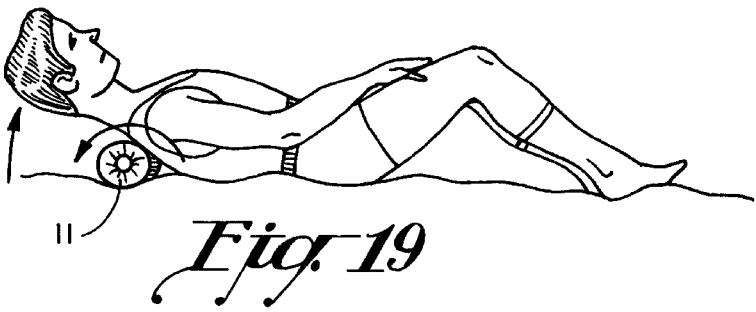
Figure 20:

In the exercise illustrated in FIGS. 18, 19 and 20, the patient is in a prone position on a soft surface similar to the exercise illustrated in FIG. 10, but with the brace positioned transverse to the spine in the cervical area. The patient then raises and lowers his or her head causing the brace 10, 11 to roll in opposite directions in the cervical area, massaging the cervical area and promoting correction of any lordosis abnormality there.

Figure 21:
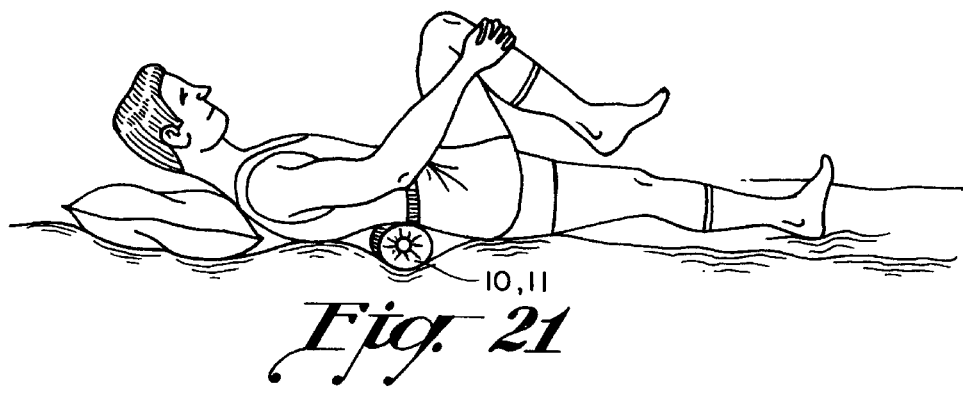
FIG. 21 illustrates the patient in a prone position utilizing the present spinal brace in a lower lumbar exercise with individual knee raises.

The exercise illustrated in FIG. 21 is the same as that illustrated in FIG. 10 with the brace 10, 11 in the lumbar area, except that the patient raises his or her legs individually with a hand grasp, promoting increased pelvic action and mobility not found in the dual leg raise exercise of FIG. 10.

It should also be understood and explained above that the braces 10, 11 can be utilized in the cervical, thoracic and lumbar areas in a static condition as opposed to the dynamic exercises as illustrated in FIGS. 10 through 21. The rigidity of the brace 10, 11 in the skeletal areas of diminished curvature promotes the return of these spinal areas to normal curvature markedly reducing pain.

I claim:

1. An orthopedic brace, comprising: a rigid base member having a generally circular outer surface, said rigid base member having a length substantially greater than its average diameter, said rigid base member being tubular in shape and having open ends substantially equal in diameter to the internal diameter of the rigid base member permitting free communication with the base member interior, resilient layer means completely encircling the base member and having portions thereof extending over and into the base member open ends, adhesive means for attaching the resilient layer means portions extending over the base member open ends to the base member open ends, said layer means having an outer body engaging generally circular surface whereby the brace may be positioned between the human body and a relatively fixed support to assist in correcting skeletal abnormalities or inadequacies, said layer means portions extending radially inwardly a substantial distance over the open ends of the rigid base, cover means surrounding the layer means and having ends that are slitted to form strips, said strips extending over the layer means portions and into the open ends of the rigid bases, said cover means holding the foam in the desired configuration.

2. An orthopedic brace as defined in claim 1, wherein the layer is synthetic foam material having a deflection factor in the range of 50 to 75.

3. An orthopedic brace as defined in claim 1, wherein the ratio of the average diameter of the base member to the overall diameter of the brace is in the range of 0.40 to 0.60.

* * * * *